(12) United States Patent
Matov et al.

(10) Patent No.: US 8,131,393 B2
(45) Date of Patent: *Mar. 6, 2012

(54) SYSTEM AND METHOD FOR AUTOMATED CONSTRUCTION OF ORTHODONTIC REFERENCE OBJECTS

(75) Inventors: Vadim Matov, San Jose, CA (US); Fuming Wu, Pleasanton, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/956,616

(22) Filed: Nov. 30, 2010

(65) Prior Publication Data
US 2011/0137626 A1    Jun. 9, 2011

Related U.S. Application Data

(62) Division of application No. 11/458,635, filed on Jul. 19, 2006, now Pat. No. 7,844,356.

(51) Int. Cl.
*G06F 19/00* (2011.01)
(52) U.S. Cl. ............. 700/98; 433/24; 433/196; 433/215
(58) Field of Classification Search ............... 700/98; 433/24, 215, 296
See application file for complete search history.

(56) References Cited

U.S. PATENT DOCUMENTS

| | | | |
|---|---|---|---|
| 5,028,232 A * | 7/1991 | Snow | 433/24 |
| 5,605,459 A | 2/1997 | Kuroda et al. | |
| 6,406,292 B1 * | 6/2002 | Chishti et al. | 433/24 |
| 6,409,504 B1 | 6/2002 | Jones et al. | |
| 6,471,511 B1 | 10/2002 | Chishti et al. | |
| 6,514,074 B1 | 2/2003 | Chishti et al. | |
| 6,767,208 B2 | 7/2004 | Kaza | |
| 6,846,179 B2 | 1/2005 | Chapouland et al. | |
| 7,063,532 B1 | 6/2006 | Jones et al. | |
| 7,474,932 B2 * | 1/2009 | Geng | 700/98 |
| 7,844,356 B2 * | 11/2010 | Matov et al. | 700/98 |
| 2002/0025503 A1 | 2/2002 | Chapoulaud et al. | |
| 2002/0028417 A1 | 3/2002 | Chapoulaud et al. | |
| 2002/0064748 A1 * | 5/2002 | Chishti et al. | 433/24 |
| 2004/0265770 A1 | 12/2004 | Chapoulaud et al. | |
| 2005/0055118 A1 | 3/2005 | Nikolskiy et al. | |
| 2006/0003292 A1 | 1/2006 | Lauren et al. | |
| 2006/0263739 A1 | 11/2006 | Sporbert et al. | |
| 2007/0003900 A1 | 1/2007 | Miller | |

FOREIGN PATENT DOCUMENTS

WO    WO 01/61613    8/2001
WO    WO 2004/098379    11/2004

* cited by examiner

*Primary Examiner* — Michael D Masinick
(74) *Attorney, Agent, or Firm* — Brooks, Cameron & Huebsch, PLLC (57) ABSTRACT

System and method for automatic construction of orthodontic reference objects, such as the occlusal plane, arch form, and the local occlusal plane for a patient's teeth are disclosed. In accordance with an exemplary embodiment, a computer-implemented system and method for automatic construction of orthodontic reference objects comprises receiving three dimensional data for the teeth, setting an initial direction for a normal of the occlusal plane, determining tips for selected teeth, calculating a plane that matches the determined tip, and determining a new normal for the calculated plane.

20 Claims, 13 Drawing Sheets

SYSTEM AND METHOD FOR AUTOMATED CONSTRUCTION OF ORTHODONTIC REFERENCE OBJECTS

PRIORITY INFORMATION

This application is a Divisional of U.S. application Ser. No. 11/458,635, filed Jul. 19, 2006, which is scheduled to issue as U.S. Pat. No. 7,844,356 on Nov. 30, 2010; the specification of which is incorporated herein by reference.

FIELD OF INVENTION

The present invention relates generally to the field of orthodontics, and in particular to system and method for automatic construction of orthodontic reference objects.

BACKGROUND OF THE INVENTION

One objective of orthodontics is to move a patient's teeth to positions where the teeth function optimally and are also aesthetically pleasing. Conventional appliances such as braces and wires are applied to the teeth of a patient by an orthodontist. Once mounted on the teeth, the braces exert continual force on the teeth and gradually urge the teeth to their respective ideal position. The orthodontist does this by adjusting the braces over time to move the teeth toward their final destination.

Orthodontic brackets are often bonded directly to the patient's teeth. Typically, a small quantity of adhesive is placed on the base of each bracket and the bracket is then placed on a selected tooth. Before the adhesive is set, the bracket is maneuvered to a desired location on the tooth. Once the adhesive has hardened, the bracket is bonded to the tooth with sufficient strength to withstand subsequent orthodontic forces as treatment progresses. One shortcoming with this technique is the difficulty in accessing the optimal surface for bracket placement on severely crowded teeth or in teeth where the bonding surface is obstructed by teeth in the opposing arch during jaw closure. With posterior teeth, the treatment provider may have difficulty seeing the precise position of the bracket relative to the tooth surface. The amount of time needed to carry out the bonding procedure may be a nuisance both to the patient as well as to the treatment provider. Also, the necessity of minimizing moisture contamination from the patient's saliva can prolong the procedure and also unduly impair the accuracy of placement of the brackets on the teeth. All of these factors increase the chance that one or more brackets will be incorrectly positioned on the teeth.

Apparatus, systems, and methods have been developed to facilitate teeth movement utilizing clear, removable teeth aligners as an alternative to braces. A mold of the patient's bite is initially taken and desired ending positions for the patient's teeth (i.e., a functionally and aesthetically optimum position) are determined, based on a prescription provided by an orthodontist or dentist. Corrective paths between the initial positions of the teeth and their desired ending positions are then planned. These corrective paths generally include a plurality of intermediate positions between the initial and ending positions of the teeth. Multiple clear, removable aligners formed to move the teeth to the various positions along the corrective path are then manufactured. One system for providing such aligners is the Invisalign® System from Align Technologies, Inc. of Santa Clara, Calif.

The planning of the corrective paths for the teeth often involves various orthodontic measurements and diagnostics. Many of these measurements utilize reference objects such as the occlusal plane, arch form, and a tooth's local occlusal plane. Thus, accurate and reliable construction of these reference objects is an important step in the planning of orthodontic treatment. Automatic construction of these reference objects would save time and eliminate human error, thus improving the accuracy of the dental measurements.

SUMMARY OF THE INVENTION

System and method for automatic construction of orthodontic reference objects, such as the occlusal plane, arch form, and the local occlusal plane for a patient's teeth are disclosed. In accordance with an exemplary embodiment, a computer-implemented system and method for automatic construction of the occlusal plane comprises receiving three dimensional data for the teeth, setting an initial direction for a normal of the occlusal plane, determining tips for selected teeth, calculating a plane that matches the determined tips, determining a new normal for the calculated plane, and repeating the steps to calculate a new plane until the difference between planes in consecutive steps is smaller than a configurable parameter.

In accordance with an exemplary embodiment, a computer-implemented system and method for automatic construction of the arch form comprises receiving three dimensional data for the patient's teeth, detecting facial axis points for the teeth, creating a plurality of pairs of corresponding teeth, calculating a mid-point for each created pair of teeth, calculating a line that approximates the calculated mid-points, utilizing the calculated line as a y-axis of a coordinate frame of the arch form, utilizing a normal of an occlusal plane as a z-axis of the coordinate frame of the arch form, determining an origin of the coordinate frame of the arch form, determining an x-axis of the coordinate frame by calculating a cross product of the y-axis and z-axis of the coordinate frame of the arch form, transforming each of the detected facial axis points into the calculated coordinate frame of the arch form, and constructing control points of a Bezier spline curve from the transformed facial axis points.

In accordance with an exemplary embodiment, a computer-implemented system and method for automatic construction of the local occlusal plane for a tooth comprises receiving three dimensional data for the tooth, setting an initial direction for a normal of the local occlusal plane, determining a tip in the direction of the normal of the local occlusal plane for each of a quadrant of the tooth, calculating a plane that matches the determined tips, determining a new normal for the calculated plane, and repeating the steps to calculate a new plane until the difference between planes in consecutive steps is smaller than a configurable parameter.

BRIEF DESCRIPTION OF THE DRAWINGS

A more complete understanding of the present invention may be derived by referring to the detailed description and claims when considered in connection with the drawing Figures, where like reference numbers refer to similar elements throughout the Figures, and:

DETAILED DESCRIPTION OF THE INVENTION

The present invention may be described herein in terms of various components and processing steps. It should be appreciated that such components and steps may be realized by any number of hardware and software components configured to perform the specified functions. For example, the present invention may employ various electronic control devices, visual display devices, input terminals and the like, which may carry out a variety of functions under the control of one or more control systems, microprocessors or other control devices. In addition, the present invention may be practiced in any number of orthodontic contexts and the exemplary embodiments relating to a system and method for automatic detection of dental features are merely a few of the exemplary applications for the invention. For example, the principles, features and methods discussed may be applied to any orthodontic treatment application.

U.S. patent application Ser. Nos. 09/264,547 and 09/311,716, now U.S. Pat. No. 6,514,074 describe techniques for generating 3-dimensional digital data sets containing models of individual components of a patient's dentition. These data sets include digital models of individual teeth and the gingival tissue surrounding the teeth. Furthermore, these applications also describe computer-implemented techniques for using the digital models in designing and simulating an orthodontic treatment plan for the patient. For example, one such technique involves receiving an initial data set that represents the patient's teeth before treatment, specifying a desired arrangement of the patient's teeth after treatment, and calculating transformations that will move the teeth from the initial to the final positions over desired treatment paths. U.S. patent application Ser. No. 09/169,276 also describes the creation of data sets representing the tooth positions at various treatment stages and the use of these data sets to produce orthodontic appliances that implement the treatment plan. One technique for producing an orthodontic appliance involves creating a positive mold of the patient's dentition at one of the treatment stages and using a conventional pressure molding technique to form the appliance around the positive mold. A design of orthodontic appliances from the digital dentition models is, for example, described in U.S. patent application Ser. No. 09/169,034.

Figure 1A:
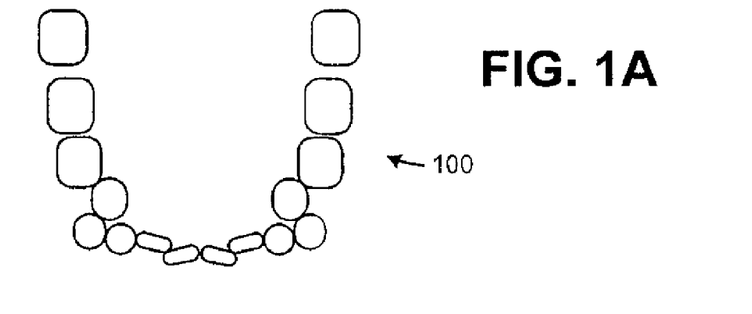
FIGS. 1A, 1B, and 1C are diagrams showing the arrangement of a patient's teeth at an initial stage, an intermediate stage, and a final stage, respectively, of orthodontic treatment.
Figure 1B:
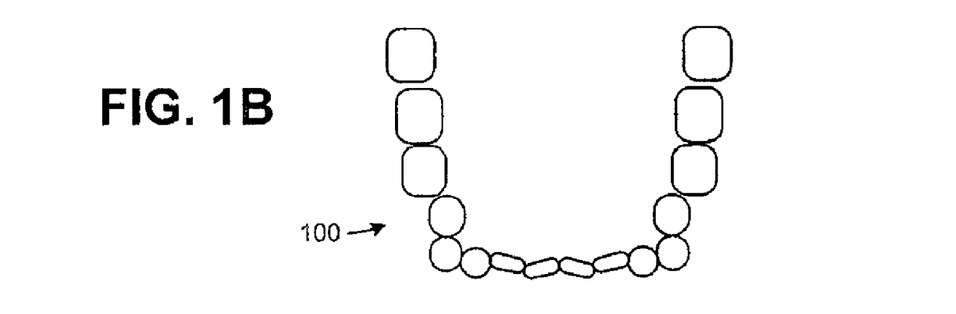
Figure 1C:
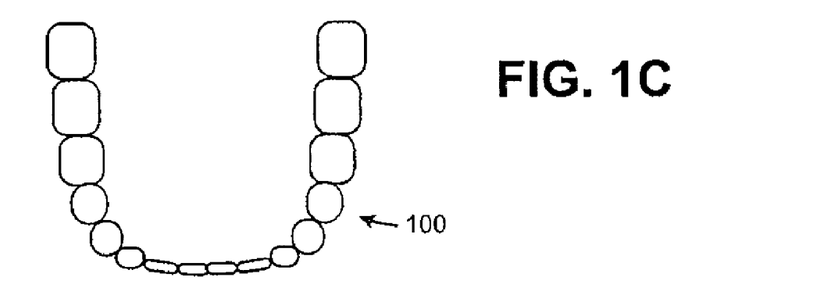

FIGS. 1A, 1B, and 1C show a patient's dentition at three stages during a course of treatment. FIG. 1A illustrates the initial positions of the patient's teeth before treatment begins. A digital model of the teeth at these initial positions is captured in an initial digital data set (IDDS).

Such an IDDS may be obtained in a variety of ways. For example, the patient's teeth may be scanned or imaged using well known technology, such as X-rays, three dimensional x-rays, computer-aided tomographic images or data sets, magnetic resonance images, and the like.

Methods for digitizing such conventional images to produce data sets are well known and described in the patent and medical literature. By way of example, one approach is to first obtain a plaster cast of the patient's teeth by well known techniques, such as those described in Graber, Orthodontics: Principle and Practice, Second Edition, Saunders, Philadelphia, 1969, pp. 401-415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set. General techniques for producing plaster casts of teeth and generating digital models using laser scanning techniques are described, for example, in U.S. Pat. No. 5,605,459. In accordance with another exemplary embodiment, the acquiring of a digital model of a patient's teeth can also comprise such techniques as disclosed in U.S. Pat. No. 6,767,208, entitled "System and Method for Positioning Teeth", assigned to Align Technology, Inc. Accordingly, any methodology or process for converting scanned data into a digital representation or otherwise for the acquiring of a digital model of a patient's teeth can be utilized.

FIG. 1B illustrates an example of how the patient's teeth may be oriented at an intermediate stage in the treatment process, and FIG. 1C illustrates an example of how the patient's teeth may be oriented at their final positions. A human operator and/or a computer program manipulate the digital models of the patient's teeth to prescribe the final tooth positions. The program then calculates one or more of the intermediate positions, taking into account any constraints imposed on the movement of the teeth by the human operator or by the natural characteristics of the teeth themselves. The program also accounts for any collisions that might occur between teeth as the teeth move from one treatment stage to the next. Selecting the final and intermediate tooth positions and the treatment paths along which the teeth move is described in more detail in one or more of the patent applications discussed above, which are all hereby incorporated by reference, in their respective entireties.

Figure 1D:
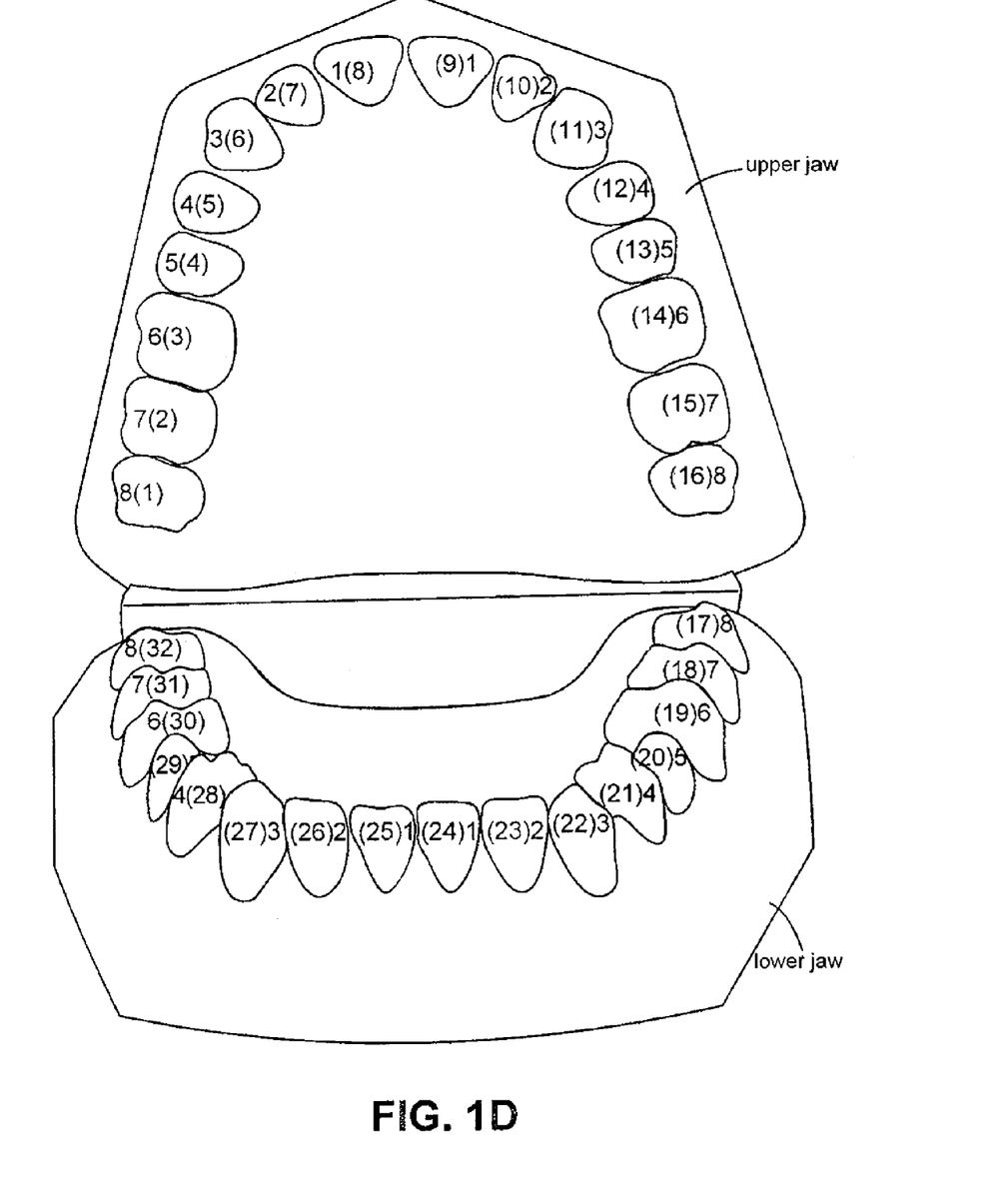
FIG. 1D is a diagram showing teeth numbering according to the standard system of tooth numbering.

FIG. 1D is a diagram of a set of teeth showing the standard system of numbering teeth. Reference is made to this standard system of numbering throughout the discussion below.

Figure 2:
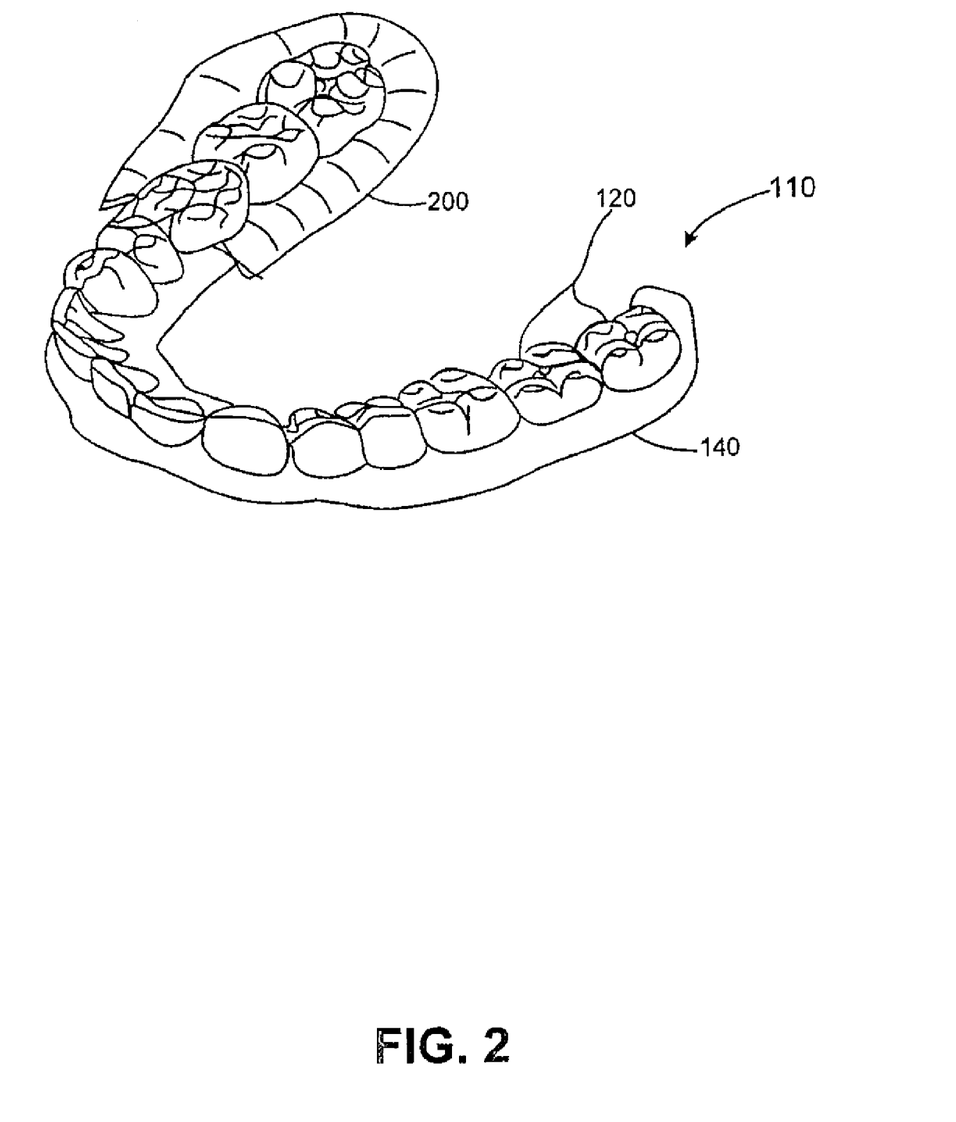
FIG. 2 is a diagram illustrating a partial model of a patient's dentition, including a model of gingival tissue.

FIG. 2 is a diagram illustrating a portion of a typical digital dentition model 110 derived from the IDDS. Dentition model 110 includes models of individual teeth 120 and a model of the patient's gums 140. Various techniques for creating models of gum tissue and individual teeth from the IDDS are described in, for example, U.S. patent application Ser. Nos. 09/264,547 and 09/311,941.

Furthermore, FIG. 2 shows a portion of another gingival model 200 (a "secondary" gingival model), which is constructed to overlie gingival model 140 derived from the IDDS (the "primary" gingival model). The program uses the secondary gingival model 200 to model the deformation of the gingival tissue around the patient's teeth as the teeth move from their initial positions to their final positions. This ensures that orthodontic appliances made from positive molds of the patient's dentition fit comfortably around the patient's gums at all treatment stages. The secondary gingival model 200 also adds thickness to the gum model, which ensures that the orthodontic appliances do not press too tightly against the patient's gums.

Reference will now be made to various exemplary embodiments of the invention, which are illustrated in the accompanying figures. While these exemplary embodiments are described in sufficient detail to enable those skilled in the art to practice the invention, it should be understood that other embodiments may be realized and that logical and/or mechanical changes may be made without departing from the spirit and scope of the invention. Thus, the various embodiments herein are presented for purposes of illustration and not by way of limitation. For example, the steps recited in any of the method or process descriptions may be executed in any order and are not limited to the order presented. Moreover, any of the functions or steps may be outsourced to or performed by one or more third parties.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical connections between the various elements. It should be noted that many alternative and/or additional functional relationships or physical connections may be present in a practical system.

Various embodiments of the present invention include one or more computing devices having programs stored therein for staging the movement of a patient's teeth. The computing device(s) or various components of any computing device discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various file indexes and/or databases used herein may include: client data; merchant data; and/or other similar useful data.

As those skilled in the art will appreciate, any computing device utilized by a user may include an operating system (e.g., Windows NT, 95/98/2000, OS2, UNIX, Linux, Solaris, MacOS, etc.) as well as various conventional support software and drivers typically associated with computers. As will be appreciated by one of ordinary skill in the art, each computing device may be embodied as a customization of an existing system, an add-on product, upgraded software, a stand alone system, a distributed system, a method, a data processing system, a device for data processing, and/or a computer program product. Accordingly, any program stored therein may take the form of an entirely software embodiment, an entirely hardware embodiment, or an embodiment combining aspects of both software and hardware. Furthermore, any program may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

In accordance with one exemplary embodiment, a computing device is configured to receive an electronic representation of the patient's teeth in an initial position taken by, for example, an intra-oral scanner or a CT scanner based on an impression or partial impression of the patient's teeth. The received data includes three dimensional data for the patient's teeth that can be used as input into the various embodiments of the present invention for automatic detection of the teeth's features. In addition, the computing device is configured to receive or generate an electronic representation of a desired final position for each of the patient's teeth. The program stored within the computing device is configured to analyze the initial and final positions, and automatically create a route for each tooth to move from its initial position to its final position. A set of aligners to move the teeth along the path in various stages is manufactured for the patient. As the patient wears the aligners, the patient's teeth move along the path according to each stage.

In order to analyze the initial, intermediate and final positions of the teeth, various orthodontic measurements and diagnostics are taken that utilize reference objects such as the occlusal plane, the arch form for the upper and lower jaw, and the local occlusal plane for specific teeth, such as the molars. Measurements of these reference objects are used to determine the corrective path for moving the patient's teeth, and can also be used to determine the final position of the teeth. In order to assist these measurements, the present invention provides for automatic construction of various orthodontic reference objects, such as the occlusal plane, arch form, and the local occlusal plane for a tooth.

Figure 3:
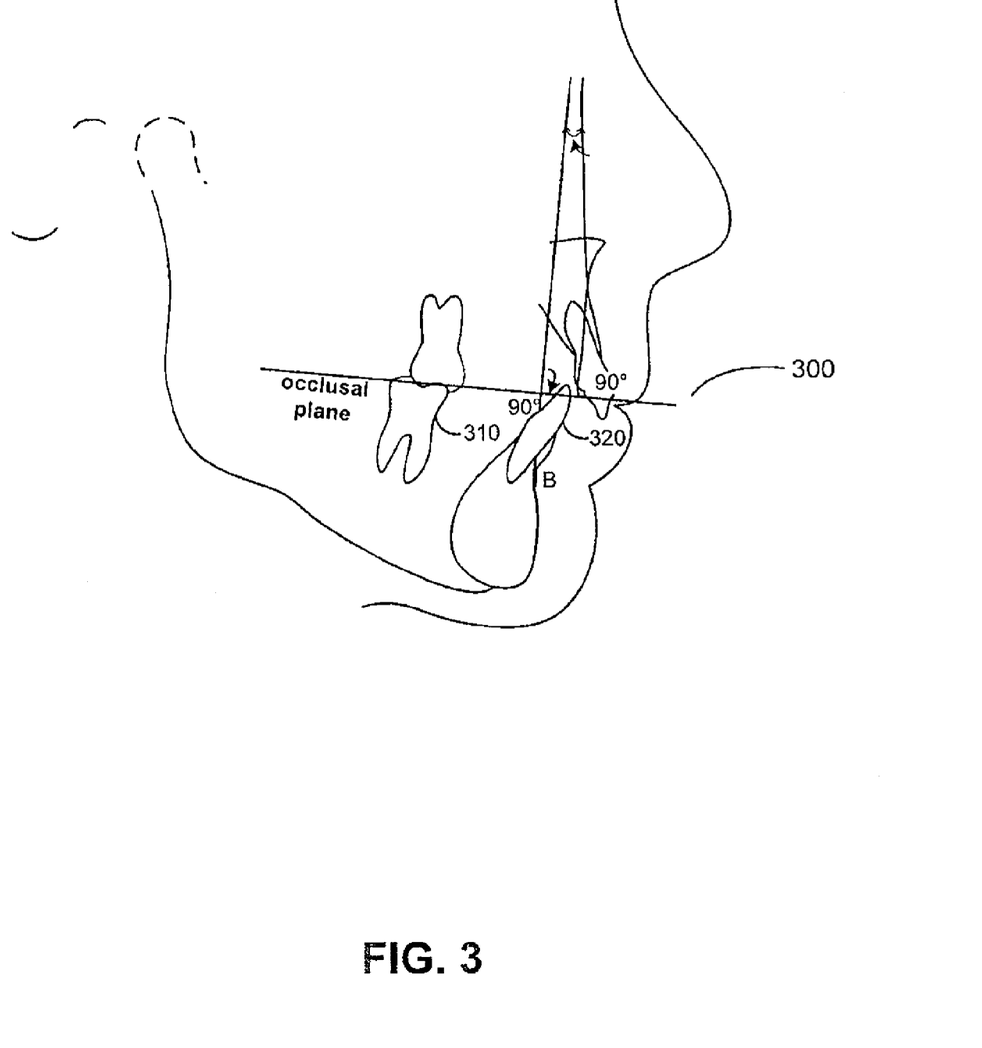
FIG. 3 illustrates an exemplary occlusal plane in accordance with an embodiment of the present invention.
Figure 10:
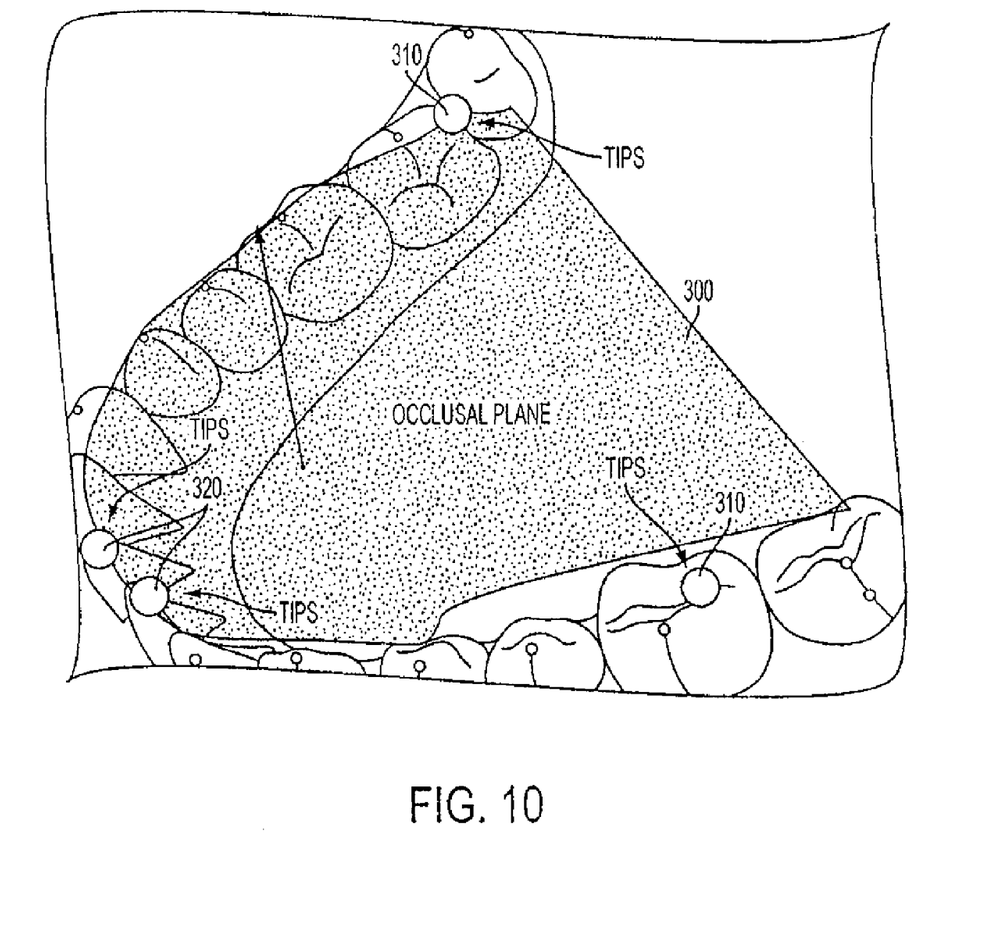
FIG. 10 illustrates an exemplary occlusal plane in accordance with an embodiment of the present invention.
Figure 11A:
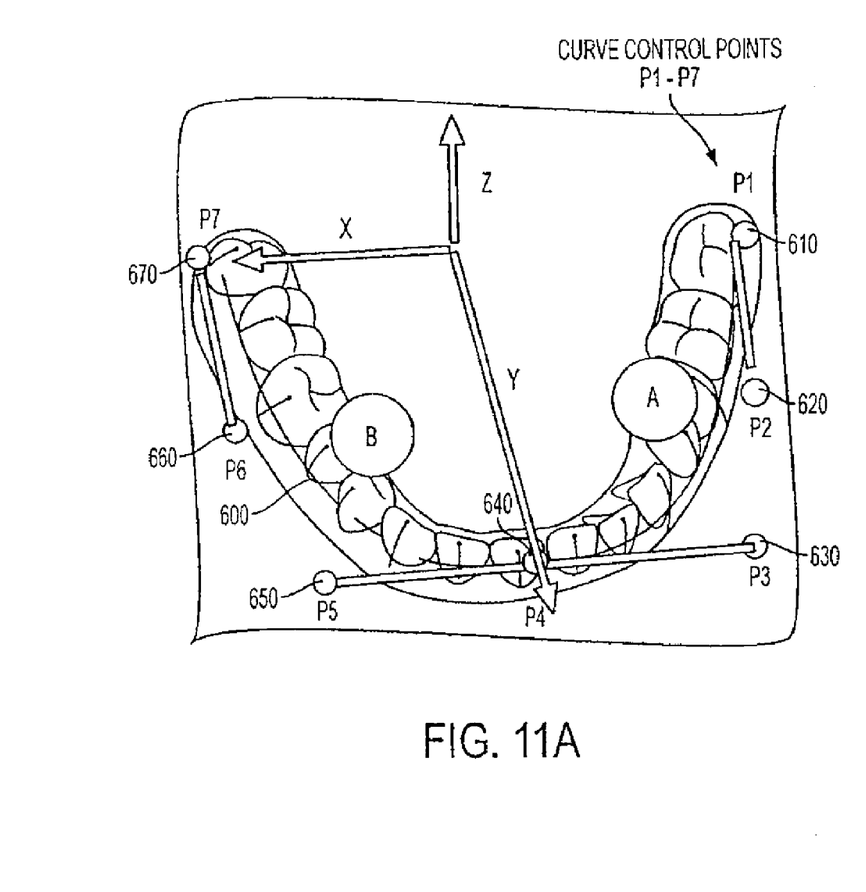
FIGS. 11A, 11B illustrate a representative Bezier spline curve that represents an exemplary arch form in accordance with an embodiment of the present invention.
Figure 11B:
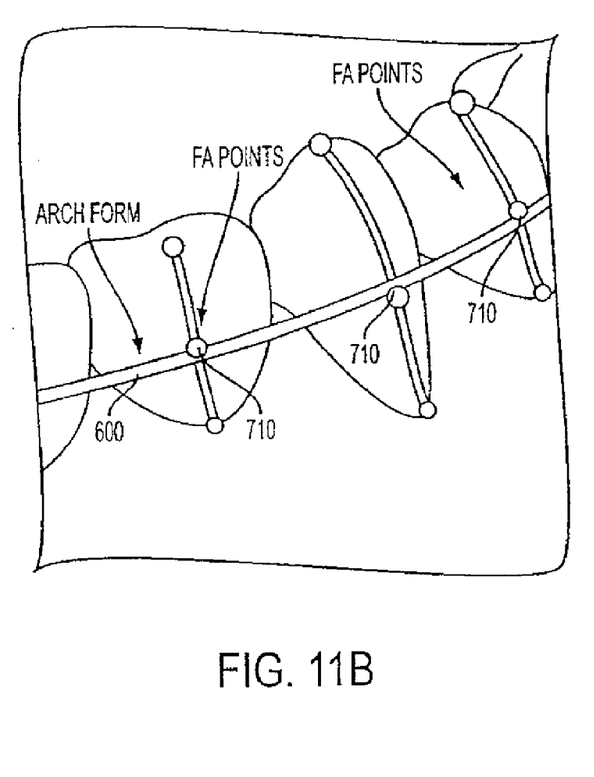

With reference to FIGS. 3 and 10, in accordance with one embodiment of the present invention, the occlusal plane 300 is the imaginary surface where the upper teeth and the lower teeth meet. For a normal bite, occlusal plane 300 will pass through the tips of lower jaw second molars 310 and the central incisors 320.

In accordance with one embodiment of the present invention, an orthogonal (i.e., x,y,z) frame of reference is used where the x-axis is aligned in the buccal-lingual direction, which is the direction between the cheek and tongue. The y-axis is aligned in the mesial-distal direction, which is the direction between the front of the mouth and the back of the mouth. The z-axis is aligned in the occlusal-root direction, which is the direction from the top of a tooth to the part of the tooth in the gum. It will be appreciated that in other embodiments of the present invention, the x-axis, y-axis, and z-axis, may be interchanged with each other or may be aligned in other orientations.

Figure 4:
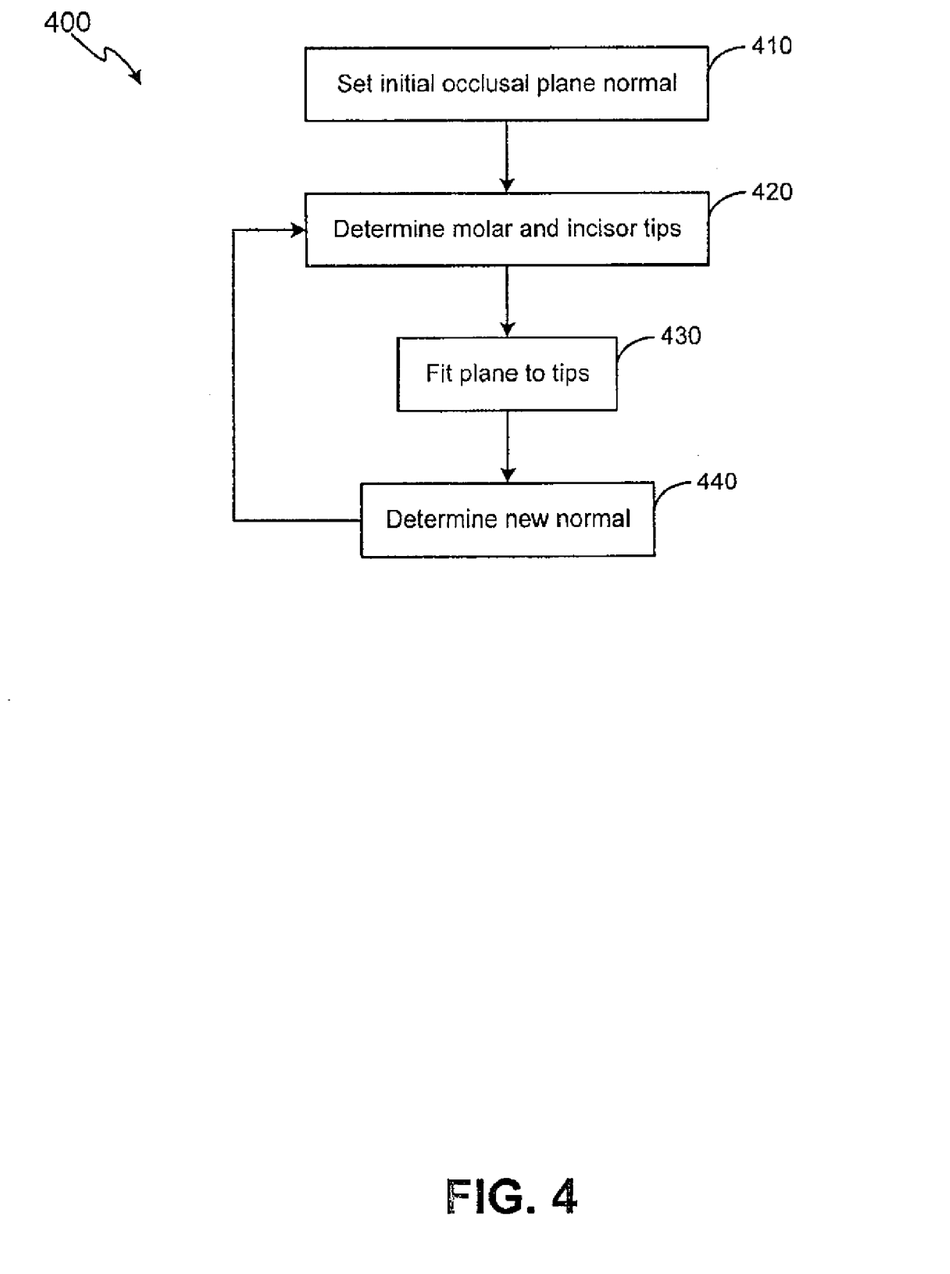
FIG. 4 illustrates an exemplary process for automatic construction of the occlusal plane in accordance with an embodiment of the present invention.

FIG. 4 is a flow diagram illustrating an exemplary process 400 for automatic construction of the occlusal plane comprising setting an initial direction for the occlusal plane normal (410), determining the tip of each of the first molars and central incisors of the lower jaw in the direction of the occlusal plane normal (420), calculating a plane that best fits the tips from step 420 (430), determining a new normal to the calculated plane from step 430 (440), repeating steps 420-440 with the new occlusal plane normal until the variation of the plane is smaller than a configurable parameter. This and other configurable parameters may be read from a computer file (e.g., parameter file) or may be entered by user in response to one or more prompts from the computer program. In accordance with one embodiment of the present invention, the z-axis is used as the initial direction of the occlusal plane normal (410). The direction of the z-axis corresponds to the direction between the top of a tooth (such as one of the lower jaw second molars) and the part of the tooth in the gum. In accordance with other embodiments of the present invention, the occlusal plane normal may have a different initial setting.

As mentioned above, input data is received in the form of three dimensional data that represents the initial position of the teeth. For each of the lower jaw first molars and central incisors, the tip of each tooth may be determined by surveying the three dimensional data and determining the highest vertex in the direction of the current occlusal plane normal (420). This will result in a set of points that represent the highest vertex for each of the teeth that have been examined. In accordance with other embodiments of the present invention, teeth other than the lower jaw first molar and central incisors may be used to calculate the occlusal plane. For example, the lower jaw second molars may be used instead of, or in addition to the lower jaw first molars. Configurable parameters to the computer program can be used to specify the particular teeth that are to be used for calculation of the occlusal plane.

Next, a plane is calculated that best matches the set of points (430) utilizing a best fit or similar method. A new occlusal plane normal can be calculated from the plane (440). Using the new occlusal plane normal, steps 420-440 are repeated with the new occlusal plane normal, until the variation between the planes in consecutive steps is smaller than a configurable parameter.

Figure 5A:
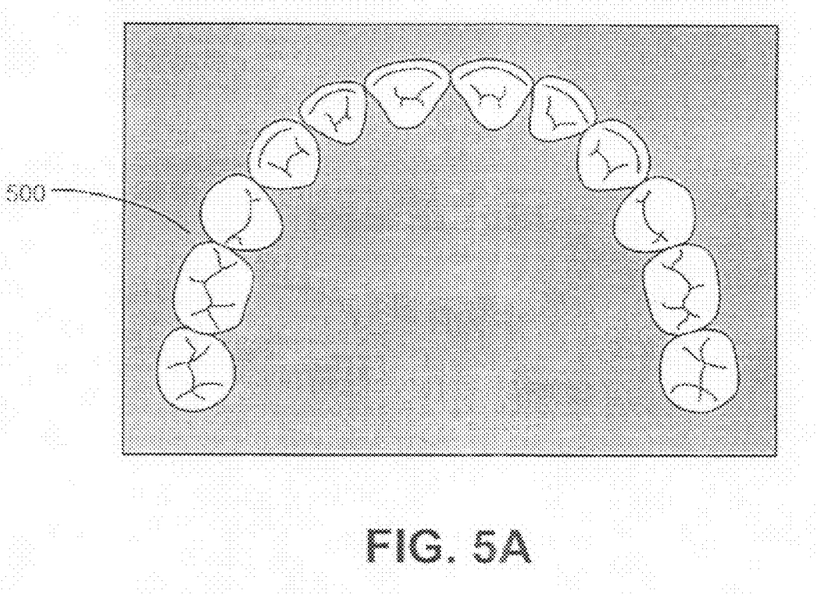
FIG. 5A illustrates a first exemplary arch form in accordance with an embodiment of the present invention.
Figure 5B:
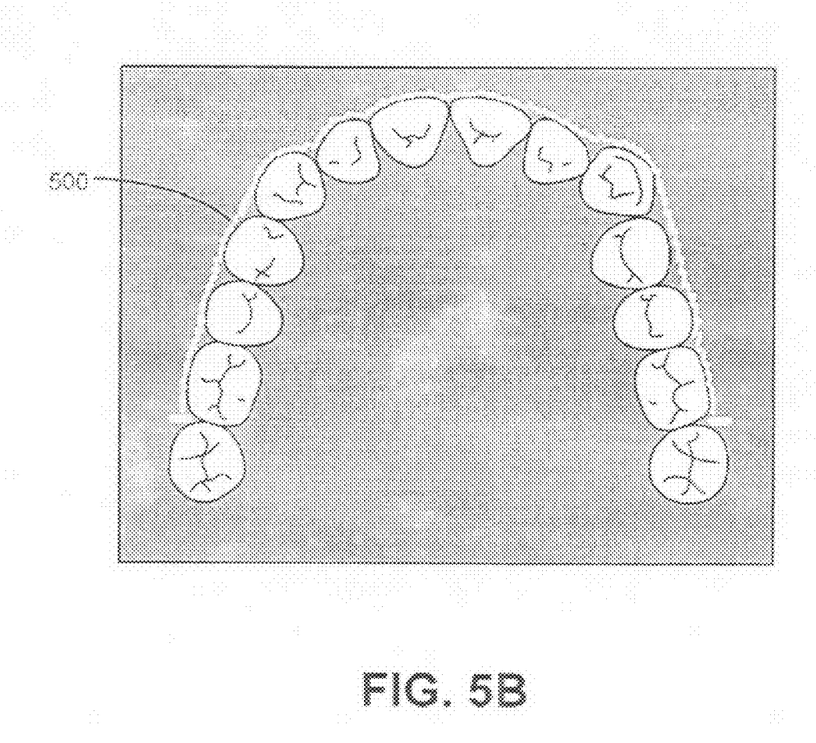
FIG. 5B illustrates a second exemplary arch form in accordance with an embodiment of the present invention.

With reference to FIG. 5A, in accordance with one embodiment of the present invention, an arch form 500 is the shape of the arch of the teeth in either the upper or lower jaw. For a normal bite, arch form 500 has a smooth, symmetric appearance. With reference to FIG. 5B, in the example of crowded or improperly located teeth, arch form 500 has a jagged, non-symmetric appearance. Many measurements such as tooth rotation and prominence are based on the arch form curve.

Figure 6:
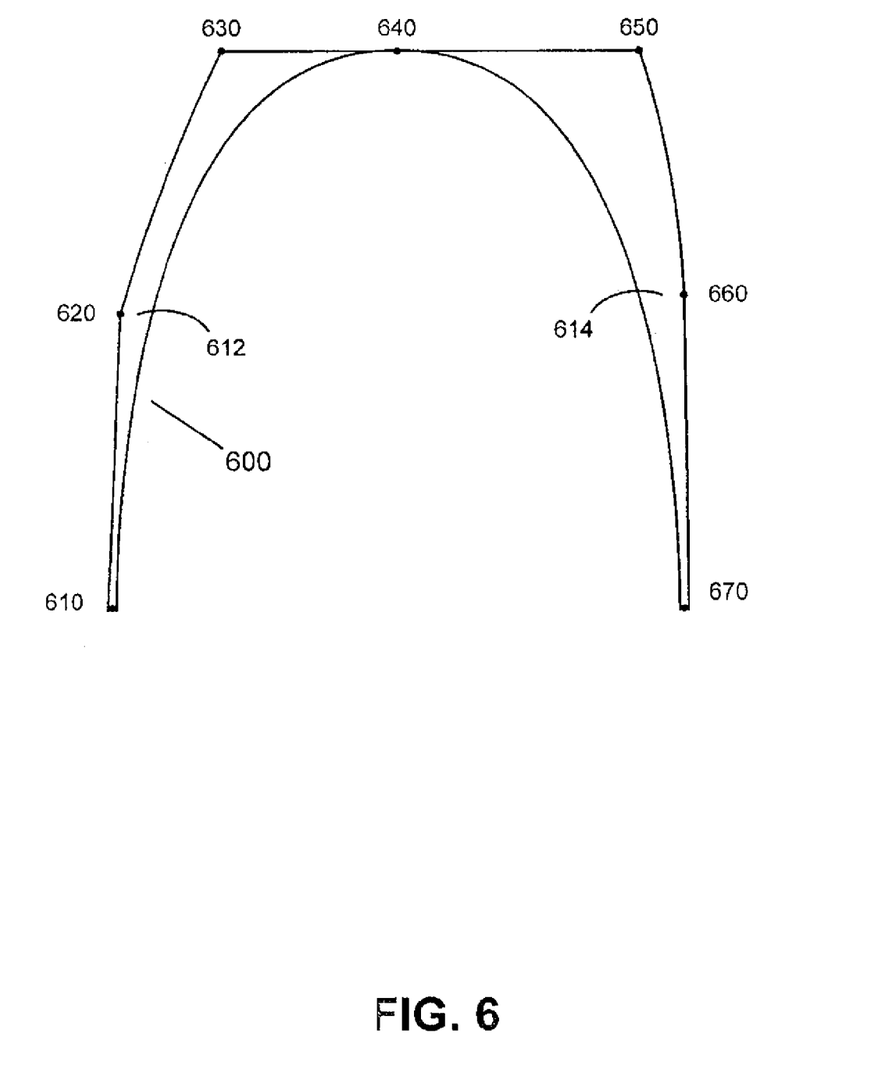
FIG. 6 illustrates a representative Bezier spline curve that represents an exemplary arch form in accordance with an embodiment of the present invention.
Figure 7:
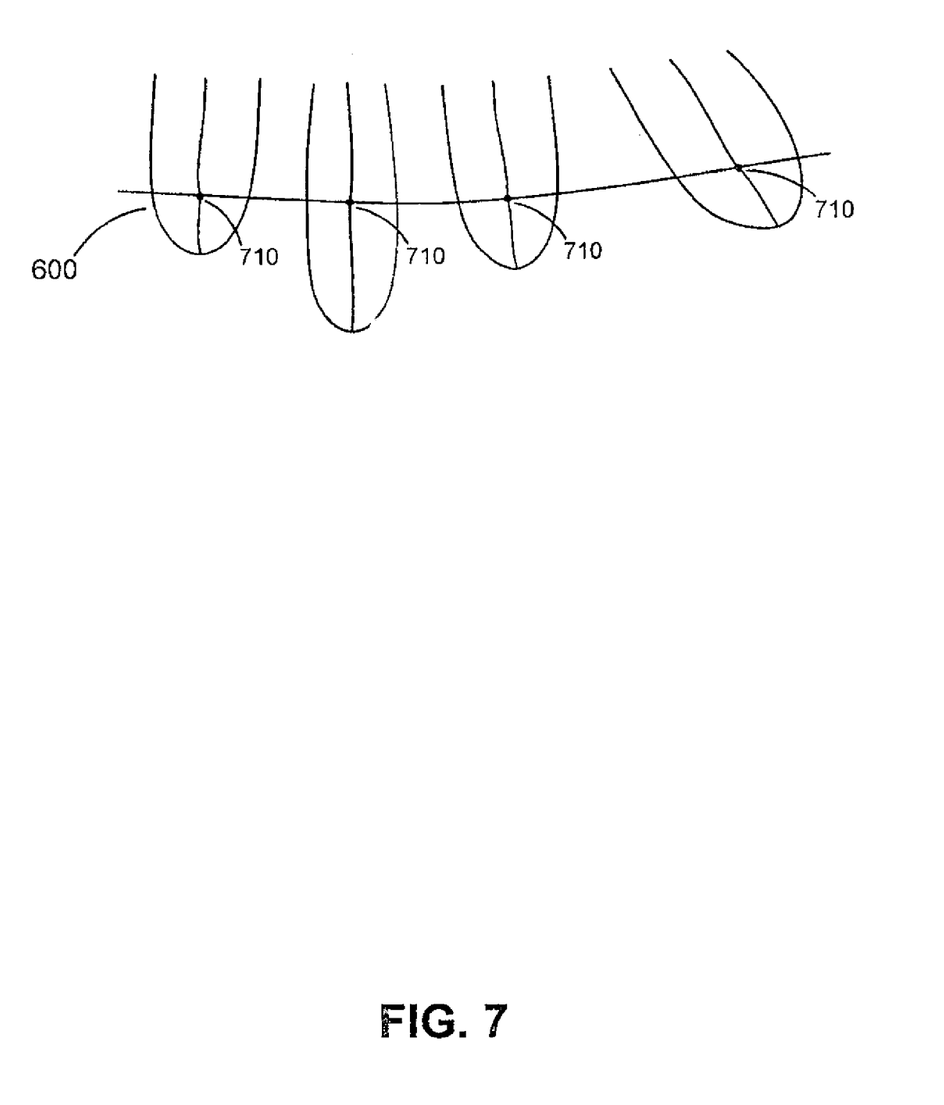
FIG. 7 illustrates a representative Bezier spline curve that represents an exemplary arch form in accordance with an embodiment of the present invention.

In accordance with an exemplary embodiment of the present invention, arch form 500 is represented by a 2-segment Bezier spline curve that passes through the midpoints of the facial axes of the clinical crown (FACC), that is FA points of the teeth. Each segment of the Bezier spline curve is a cubic curve with four control points. With reference to FIGS. 6-7 and 11A-B, a representative 2-segment Bezier spline curve 600 is illustrated that represents an exemplary arch form that passes through FA points 710. In the example of FIG. 6, Bezier spline curve 600 is constructed from two segments 612, 614. Control points 610, 620, 630, 640 are used to construct segment 612, and control points 640, 650, 660, 670 are used to construct segment 614. Bezier spline curve 600 is formed by approximating a curve that passes through control points 610-670.

Figure 8:
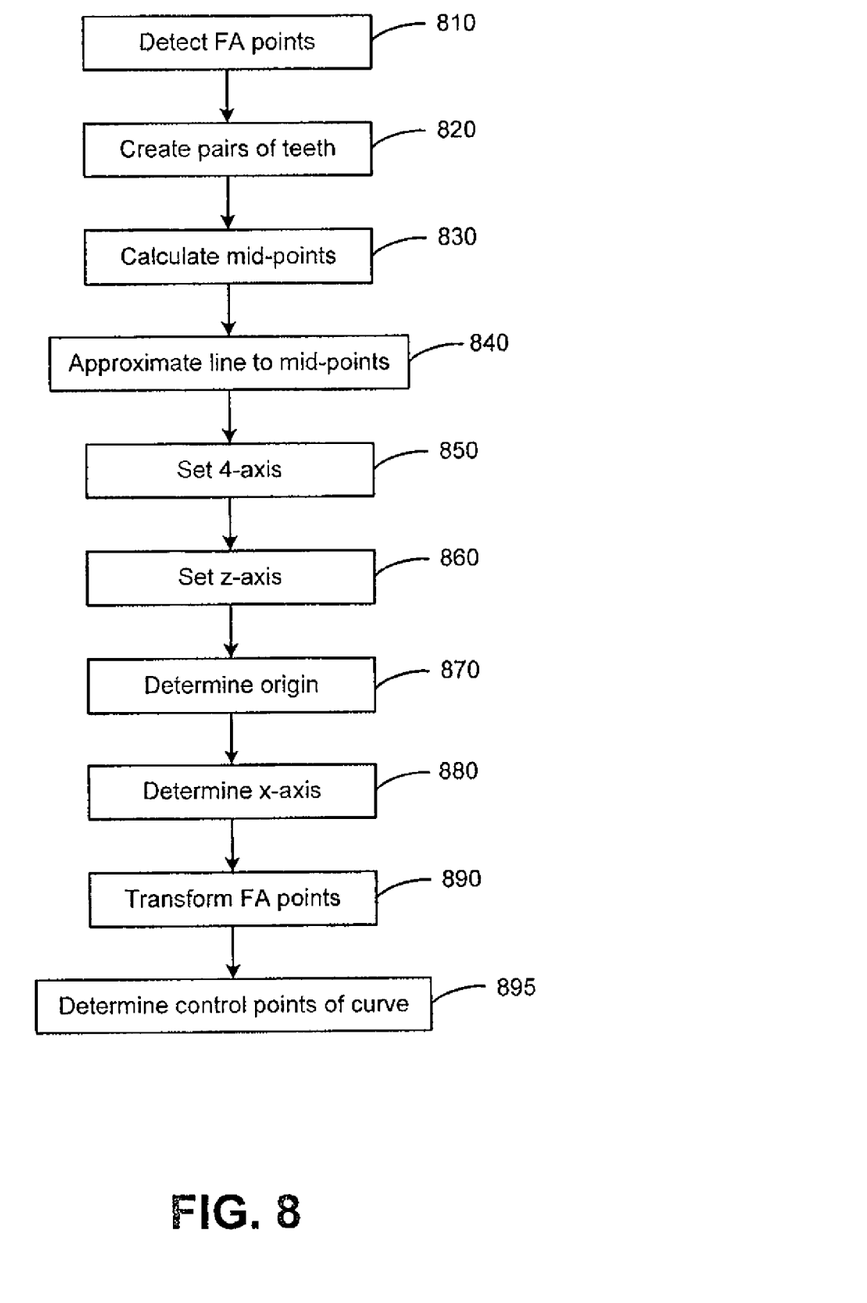
FIG. 8 illustrates an exemplary process for automatic construction of the arch form in accordance with an embodiment of the present invention.

As mentioned above, input data is received in the form of three dimensional data that represents the initial position of the teeth. FIG. 8 is a flow diagram illustrating an exemplary process for automatic construction of the arch form. In accordance with one embodiment of the present invention, utilizing the received three dimensional data, a process for automatic construction of the arch form includes detecting FA points for the teeth of the upper or lower jaw (810), creating pairs of corresponding teeth (820), calculating a mid-point for each pair of teeth (830), calculating a line that approximates the calculated mid-points (840), utilizing the calculated line as the y-axis of a coordinate frame of the arch form (850), utilizing the normal vector to the occlusal plane 300 as the z-axis of the coordinate frame of the arch form (860), determining the mid-point of the second molars for the origin of the coordinate frame of the arch form (870), using the cross product of the y-axis and z-axis for the x-axis of the coordinate frame of the arch form (880), transforming each of the detected FA points into the calculated coordinate frame of the arch form (890), and using a least square algorithm to determine the control points of the Bezier spline curve of the arch form (895).

FA points are detected (810) for the teeth of either the upper or lower arch. In accordance with one embodiment of the present invention, FA points may be detected by determining the Facial Axis centers for all crowns of teeth.

Pairs of corresponding teeth are created (820) for teeth on the left and right side of the arch. For example, the left second molar is paired with the right second molar. For each pair of teeth, a mid-point of a line between the teeth is calculated (830). In accordance with one embodiment of the present invention, the line between the FA points of the pair of teeth is used for calculating the mid-point. Other embodiments of the present invention may utilize other parts of the teeth such as the tips of the teeth.

Next, a line is calculated that approximates the calculated mid-points (840). The calculated line may treat each calculated mid-point equally, or certain of the mid-points may be weighted such that the weighted mid-points have more of an effect on the final location of the line. This line may be used as the y-axis of a coordinate frame of the arch form (850). In accordance with other embodiments of the present invention, the line may be used as another axis of the arch form such as the x-axis or z-axis.

The normal to occlusal plane 300 may be used as the z-axis of the coordinate frame of the arch form (860). Similarly, in accordance with other embodiments of the present invention, the normal to occlusal plane 300 may be used as another axis of the arch form such as the x-axis or y-axis.

The middle point for the second molars may be used as the origin of the coordinate frame (870). That is, the mid-point for a line connecting the FA points of the second molars may be used as the origin of the coordinate frame of the arch form. Other embodiments of the present invention may utilize the mid-point of the line connecting the tips of the second molars as the origin of the coordinate frame. Other embodiments may utilize the mid-point of the line connecting the first molars as the origin of the coordinate frame of the arch form.

The x-axis of the coordinate frame may be determined from the cross product of the y-axis and the z-axis (step 880).

All FA points are transformed into the newly calculated x-y-z coordinate frame (step 890) such that the FA points are in the same coordinate system of the constructed arch form. Finally, a least square algorithm may be used to find the control point of Bezier spine curve (895) from the transformed FA points. As stated above, the calculated Bezier spine curve represents the arch form for the teeth of the arch.

Figure 9:
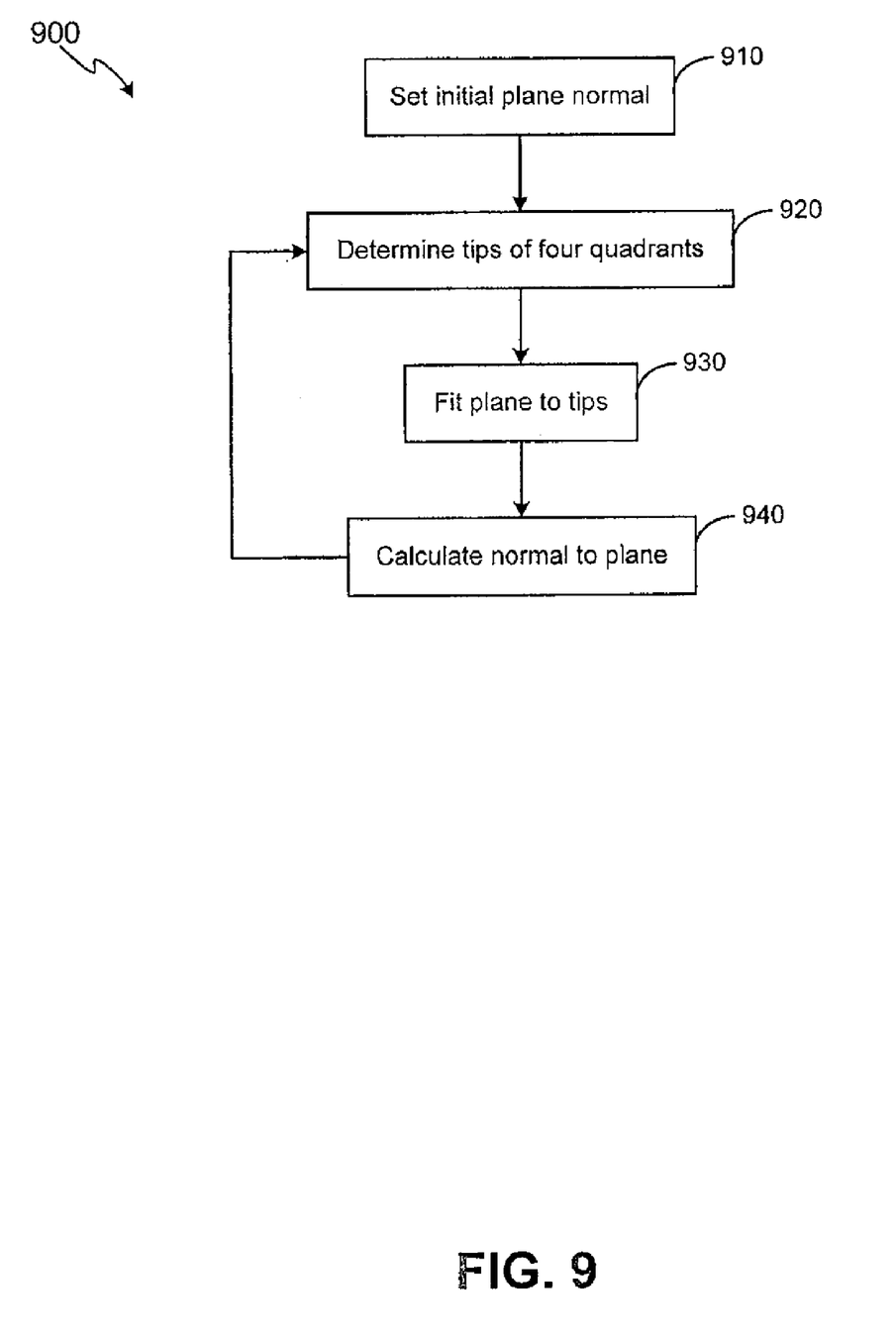
FIG. 9 illustrates an exemplary process for automatic construction of a local occlusal plane in accordance with an embodiment of the present invention.

FIG. 9 is a flow diagram illustrating an exemplary process 900 for automatic construction of a local occlusal plane for a tooth such as a first or second molar. An exemplary process comprises setting an initial direction for the local occlusal plane normal (910), determining the tip, in the direction of the local occlusal plane normal, for each of the four quadrants defined by the tooth frame of reference (920), calculating a plane that best fits the tips (930), calculating a normal of the calculated plane, and repeating steps 920-940 with the new local occlusal plane normal until the variation of the plane is smaller than a configurable parameter. In accordance with one embodiment of the present invention, the vertical axis of the tooth is used as the initial direction of the local occlusal plane normal (910). The vertical axis corresponds to the direction between the top of the tooth to the part of the tooth in the gum. In accordance with other embodiments of the present invention, the occlusal plane normal may have a different initial setting.

Figure 12:
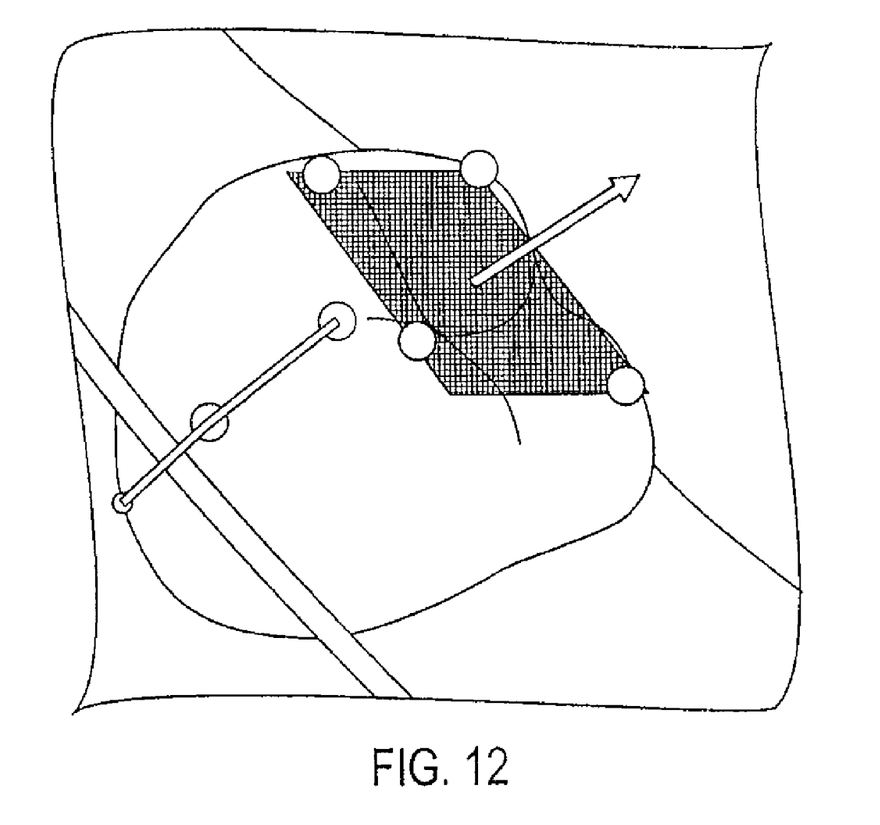
FIG. 12 illustrates an exemplary local occlusal plane in accordance with an embodiment of the present invention.

With reference to FIG. 12, for each of the four quadrants of the tooth, the tip of each quadrant may be determined by surveying the three dimensional data and determining the highest vertex in the direction of the current local occlusal plane normal (920). This will result in a set of points that represent the highest vertex for each quadrant of the tooth being examined.

Next, a plane is calculated that best matches the set of tips (930) utilizing a means square approach or similar method. A new local occlusal plane normal can be calculated from the plane (940). Using the new local occlusal plane normal, steps 920-940 are repeated with the new local occlusal plane normal, until the variation between the planes on consecutive steps is smaller than a configurable parameter.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims.

We claim:

1. A computer-implemented method for automatic construction of a local occlusal plane for a patient's tooth, comprising:
   a) receiving three dimensional data for the patient's tooth;
   b) setting an initial direction for determining a tip of the patient's tooth, the initial direction being a vertical axis of the tooth between a top of the patient's tooth and a root of the patient's tooth in the patient's gums;
   c) determining a tip, based on the initial direction, for each of a quadrant of the patient's tooth;
   d) calculating a local occlusal plane that best fits the determined tips;
   e) determining a normal for the calculated local occlusal plane;
   f) determining a new tip, based on the normal, for each quadrant of the patient's tooth; and
   g) calculating a new local occlusal plane that best fits the determined new tips;
   wherein steps (a)-(g) are performed by a computer.

2. The computer-implemented method of claim 1, wherein the step of setting an initial direction comprises using a z-axis as the initial direction.

3. The computer-implemented method of claim 2, wherein the z-axis corresponds to a direction between the top of the patient's tooth and the root of the patient's tooth.

4. The computer-implemented method of claim 1, wherein the step of determining the tip comprises:
   examining the three dimensional data for each of the four quadrants of the tooth; and
   determining a highest point for each of the quadrants in the initial direction.

5. The computer-implemented method of claim 1, wherein the method further includes:
   h) determining a new normal for the calculated new local occlusal plane.

6. The computer-implemented method of claim 5, further comprising repeating steps (f)-(h) until a variation between the new local occlusal planes on consecutive steps is smaller than a configurable parameter.

7. The computer-implemented method of claim 5, further comprising repeating steps (f)-(h) until a variation between the new local occlusal plane and the determined new tips is smaller than a configurable parameter.

8. The computer-implemented method of claim 5, wherein the method includes repeating at least steps (f)-(g).

9. A computerized system for automatic construction of a local occlusal plane for a patient's tooth, the computerized system comprising:
   a microprocessor comprising a plurality of algorithms;
   a memory device; and
   wherein the computerized system is configured for:
      a) receiving three dimensional data for the patient's tooth;
      b) setting an initial direction for determining a tip of the patient's tooth, the initial direction being a vertical axis of the tooth between a top of the patient's tooth and a root of the patient's tooth in the patient's gums;
      c) determining a tip, based on the initial direction, for each of a quadrant of the patient's tooth;
      d) calculating a local occlusal plane that best fits the determined tips;
      e) determining a normal for the calculated local occlusal plane;
      f) determining a new tip, based on the normal, for each quadrant of the patient's tooth; and
      g) calculating a new local occlusal plane that best fits the determined new tips.

10. The computerized system of claim 9, wherein the computerized system is further configured for:
    h) determining a new normal for the calculated new local occlusal plane.

11. The computerized system of claim 10, wherein the computerized system is further configured for repeating steps (f)-(h) until a variation between the new local occlusal planes on consecutive steps is smaller than a configurable parameter.

12. The computerized system of claim 10, wherein the computerized system is further configured for repeating steps (f)-(h) until a variation between the new local occlusal plane and the determined new tips is smaller than a configurable parameter.

13. The computerized system of claim 10, wherein the computerized system is further configured for repeating at least steps (f)-(g).

14. The computerized system of claim 9, wherein the step of determining the tip comprises:
    examining the three dimensional data for each of the four quadrants of the tooth; and
    determining a highest point for each of the quadrants in the initial direction.

15. A non-transitory computer-readable storage medium having computer-readable program code, which when executed by a computer, causes the computer to automatically construct a local occlusal plane for a patient's tooth by:
    a) receiving three dimensional data for the patient's tooth;
    b) setting an initial direction for determining a tip of the patient's tooth, the initial direction being a vertical axis of the tooth between a top of the patient's tooth and a root of the patient's tooth in the patient's gums;
    c) determining a tip, based on the initial direction, for each of a quadrant of the patient's tooth;
    d) calculating a local occlusal plane that best fits the determined tips;

e) determining a normal for the calculated local occlusal plane;
f) determining a new tip, based on the normal, for each quadrant of the patient's tooth; and
g) calculating a new local occlusal plane that best fits the determined new tips.

16. The medium of claim 15, wherein the code causes the computer to automatically construct a local occlusal plane by further:
h) determining a new normal for the calculated new local occlusal plane.

17. The medium of claim 16, wherein the code causes the computer to automatically construct a local occlusal plane by further repeating steps (f)-(h) until a variation between the new local occlusal planes on consecutive steps is smaller than a configurable parameter.

18. The medium of claim 16, wherein the code causes the computer to automatically construct a local occlusal plane by further repeating steps (f)-(h) until a variation between the new local occlusal plane and the determined new tips is smaller than a configurable parameter.

19. The medium of claim 16, wherein the code causes the computer to automatically construct a local occlusal plane by further repeating at least steps (f)-(g).

20. The medium of claim 16, wherein the step of determining the tip comprises:
examining the three dimensional data for each of the four quadrants of the tooth; and
determining a highest point for each of the quadrants in the initial direction.

* * * * *